United States Patent [19]
Veber et al.

[11] Patent Number: 4,478,826
[45] Date of Patent: Oct. 23, 1984

[54] RENIN INHIBITORY PEPTIDES

[75] Inventors: Daniel F. Veber, Ambler; Joshua S. Boger, Bryn Mawr, both of Pa.

[73] Assignee: Merck & Co., Inc., Rahway, N.J.

[21] Appl. No.: 413,633

[22] Filed: Sep. 3, 1982

Related U.S. Application Data

[63] Continuation-in-part of Ser. No. 309,855, Oct. 8, 1981.

[51] Int. Cl.³ .................... C07C 103/52; A61K 37/02
[52] U.S. Cl. .............................. 424/177; 260/112.5 R
[58] Field of Search .................. 260/112.5 R; 424/177

[56] References Cited

U.S. PATENT DOCUMENTS

| | | | |
|---|---|---|---|
| 3,784,686 | 1/1974 | Miller | 424/94 |
| 3,873,681 | 3/1975 | Müller | 424/94 |
| 4,185,096 | 1/1980 | Castero et al. | 424/177 |
| 4,269,827 | 5/1981 | Burton et al. | 424/177 |
| 4,384,994 | 5/1983 | Veber et al. | 424/177 |

FOREIGN PATENT DOCUMENTS 51-67001  6/1976  Japan .

OTHER PUBLICATIONS

Kund et al., *Biochem. Biophys. Acta*, 452(2), 533-537 (1976).
Powers et al., *Acid Proteases, Structure, Function and Biology*, Plenum Press 1977, 141-157.
*Trends in Biochem. Sci.*, 1, 205-208(1976).

*Primary Examiner*—Delbert R. Phillips
*Assistant Examiner*—F. T. Moezie
*Attorney, Agent, or Firm*—Raymond M. Speer; Hesna J. Pfeiffer

[57] ABSTRACT

Renin inhibitory peptides of the formula

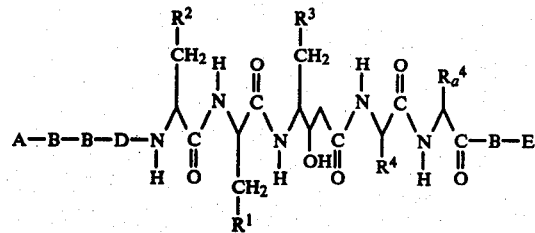

and analogs thereof inhibit renin and are useful for treating various forms of renin-associated hypertension and hyperaldosteronism.

19 Claims, No Drawings

RENIN INHIBITORY PEPTIDES

REFERENCE TO RELATED APPLICATIONS

This is a continuation-in-part in application Ser. No. 309,855, filed Oct. 8, 1981.

BACKGROUND OF THE INVENTION

1. Field of the Invention

The present invention is concerned with novel peptides which inhibit renin.

The present invention is also concerned with pharmaceutical compositions containing the novel peptides of the present invention as active ingredients, with methods of treating renin-associated hypertension and hyperaldosteronism, with diagnostic methods which utilize the novel peptides of the present invention, and with methods of preparing the novel peptides of the present invention.

Renin is a proteolytic enzyme of molecular weight about 40,000, produced and secreted by the kidney. It is secreted by the juxtaglomerular cells and acts on the plasma substrate, angiotensinogen, to split off the decapeptide angiotensin I, which is converted to the potent pressor agent angiotensin II. Thus, the renin-angiotensin system plays an important role in normal cardiovascular homeostasis and in some forms of hypertension.

In the past, attempts to modulate or manipulate the renin-angiotensin system have met with success in the use of inhibitors of angiotensin I converting enzyme. In view of this success, it seems reasonable to conclude that a specific inhibitor of the limiting enzymatic step that ultimately regulates angiotensin II production, the action of renin on its substrate, would be at least equally successful. Thus, an effective inhibitor of renin has been long sought as both a therapeutic agent and as an investigative tool.

2. Brief Description of the Prior Art

There has been substantial interest in the synthesis of useful renin inhibitors for many decades; and the following table lists the major classes of renin inhibitors that have been studied, as well as their inhibition constants ($K_I$):

| Class | $K_I$ (M) |
|---|---|
| Renin antibody | probably $10^{-6}$ |
| Pepstatin | $10^{-6}$–$10^{-7}$ |
| Phospholipids | $10^{-3}$ |
| Substrate analogs | |
| Tetrapeptides | $10^{-3}$ |
| Octa- to tridecapeptides | $10^{-5}$–$10^{-6}$ |

Umezawa et al., in *J. Antibiot.* (Tokyo) 23: 259-262, 1970, reported the isolation of a peptide from actinomyces that was an inhibitor of aspartyl proteases such as pepsin, cathepsin D, and renin. This peptide, known as pepstatin, was found by Gross et al., *Science* 175:656, 1971, to reduce blood pressure in vivo after the injection of hog renin into nephrectomized rats. However, pepstatin has not found wide application as an experimental agent because of its limited solubility and its inhibition of a variety of other acid proteases in addition to renin. The structure of pepstatin is shown below:

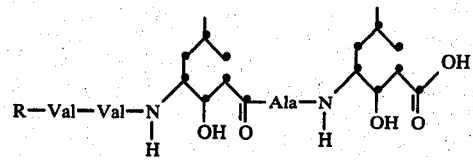

To date, many efforts have been made to prepare a specific renin inhibitor based on substrate analogy. Since the human renin substrate has only recently been elucidated (Tewksbury et al., *Circulation* 59, 60, Supp. II: 132, Oct. 1979), heretofore substrate analogy has been based on the known pig renin substrate. While the human and pig renin substrates are not the same, the substrate analogy based on pig renin has always been considered acceptable in the art as predictive of human renin inhibitory activity because of the closely related activity of the two renins. Thus, while pig renin does not cleave the human renin substrate, human renin, on the other hand, does cleave the pig renin substrate. See Poulsen et at., *Biochim. Biophys. Acta* 452:533-537, 1976; and Skeggs, Jr. et al., *J. Exp. Med.* 106: 439-453, 1957. Moreover, the human renin inhibitory activity of the peptides of the present invention most active in inhibiting pig renin has been confirmed, thus providing further evidence of this accepted correlation between human and pig renin activity.

It has been found, for example, using pig renin substrate analogy, that the octapeptide sequence extending from histidine-6 through tyrosine-13 has kinetic parameters essentially the same as those of the full tetradecapeptide renin substrate. The amino acid sequence of the octapeptide in pig renin substrate is as follows:

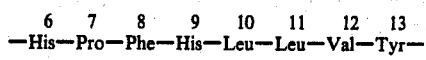

Renin cleaves this substrate between Leu[10] and Leu[11].

Kokubu et al., *Biochem. Pharmacol.* 22: 3217-3223, 1973, synthesized a number of analogs of the tetrapeptide found between residues 10 to 13, but while inhibition could be shown, inhibitory constants were only of the order of $10^{-3}$M.

Analogs of a large segment of renin substrate were also synthesized: Burton et al., *Biochemistry* 14: 3892-3898, 1975, and Poulsen et al., *Biochemistry* 12: 3877-3882, 1973. Two of the major obstacles which had to be overcome to obtain an effective renin inhibitor useful in vivo were lack of solubility and weak binding (large inhibitory constant). Modifications to increase solubility soon established that the inhibitory properties of the peptides are markedly dependent on the hydrophobicity of various amino acid residues, and that increasing solubility by replacing lipophilic amino acids with hydrophilic isosteric residues becomes counterproductive. Other approaches to increasing solubility have had limited success. Various modifications designed to increase binding to renin have also been made, but here too, with only limited success. For a more detailed description of past efforts to prepare an effective inhibitor of renin, see Haber and Burton, *Fed. Proc. Fed. Am. Soc. Exp. Biol.* 38: 2768-2773, 1979.

For other articles describing previous efforts to devise renin inhibitors, see Marshall, *Federation Proc.* 35: 2494-2501, 1976; Burton et al., *Proc. Natl. Acad. Sci. USA* 77: 5476-5479, September 1980; Suketa et al., *Bio-*

*chemistry* 14: 3188, 1975; Swales, *Pharmac. Ther.* 7: 173-201, 1979; Kokubu et al., *Nature* 217: 456-457, Feb. 3, 1968; Matsushita et al., *J. Antibiotics* 28: 1016-1018, December 1975; Lazar et al., *Biochem. Pharma.* 23: 2776-2778, 1974; Miller et al., *Biochem. Pharma.* 21: 2941-2944; 1972; Haber, *Clinical Science* 59: 7s-19s, 1980; and Rich et al., *J. Org. Chem.* 43: 3624, 1978, and *J. Med. Chem.* 23: 27, 1980.

DETAILED DESCRIPTION OF THE INVENTION AND PREFERRED EMBODIMENTS

In accordance with the present invention there are provided renin inhibitory peptides of the formula:

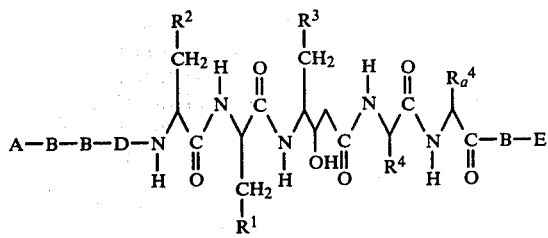

wherein:
A is hydrogen;

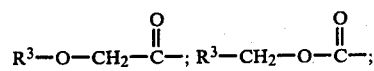

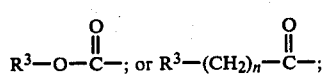

where n is 0 to 5 and $R^3$ has the same meaning as set out further below, and may additionally be hydrogen;
B is absent; glycyl; sarcosyl; or

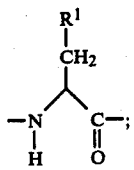

D is absent; or

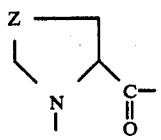

where Z is $(CH_2)_n$ and n is 1 or 2; or —S—;
$R^1$ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl;
$R^2$ is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;
$R^3$ is $C_{3-6}$ alkyl; $C_{3-7}$ cycloalkyl; phenyl; or phenyl mono-substituted with a member selected from the group consisting of methyl, trifluoromethyl, hydroxy, methoxy, fluoro, chloro, bromo, and iodo;
$R^4$ and $R_a^4$ are independently hydrogen; or

where $R^5$ is hydrogen; $C_{1-4}$ alkyl; hydroxy; or $C_{3-7}$ cycloalkyl; and
E is OR; NHR, or $N(R)_2$, where each R may be the same or different and is hydrogen or $C_{1-4}$ alkyl;
wherein all of the asymmetric carbon atoms have an S configuration, except those of substituents B and D, which may also have the R configuration; and a pharmaceutically acceptable salt thereof.

In the above definitions, the term "alkyl" is intended to include both branched and straight chain hydrocarbon groups having the indicated number of carbon atoms.

The novel renin inhibitory peptides of the present invention may also be described in terms of common amino acid components and closely related analogs thereof, in accordance with the following formula:

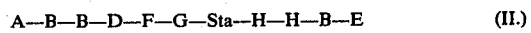

A—B—B—D—F—G—Sta—H—H—B—E    (II.)

The A,B,D, and E components correspond to the same portions of Formula I.

In Formula II, Sta represents the unusual amino acid statine and its closely related analogs, and its presence constitutes a unique feature of the renin inhibitory peptides of the present invention. Statine may be named as 4(S)-amino-3(S)-hydroxy-6-methylheptanoic acid, and may be represented by the following formula:

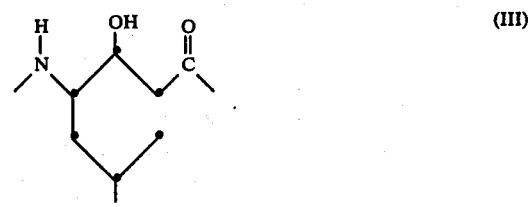

As shown in Formula III above, the delta-substituent in naturally-occurring statine is isopropyl, or a leucine sidechain, essentially. As shown in Formula I by the $R^3$ substituents, the isopropyl group may be replaced by higher alkyl groups up to six carbon atoms, cycloalkyl groups containing from three to seven carbon atoms, phenyl, and phenyl mono-substituted with a member selected from the group consisting of methyl, trifluoromethyl, hydroxy, methoxy, fluoro, chloro, bromo, and iodo. The phenyl substituent is especially preferred. These modifications of the naturally-occurring statine structure are in accordance with the hydrophobicity considered necessary to maintain the inhibitory activity of the total peptide.

The remaining common amino acid components of Formula II are as follows:
A has the same meaning as above in Formula I;
B is absent, Gly, Ala, Val, Leu, Ile, Phe, Tyr, Trp, His, Lys, Orn, Arg, or Met;
D is absent or Pro;
F is Ala, Leu, Phe, Tyr, or Trp;

G is Ala, Leu, Phe, Tyr, Trp, His, Lys, Orn, Arg, or Met;

H is the same as F and may additionally be Ser, Gly, Val, Ile, or Thr; and

E has the same meaning as above in Formula I.

It will be understood that closely related analogs of the above common amino acids, for example, aliphatic amino acids in addition to Ala, Val, Leu, and Ile, such as α-aminobutyric acid (Abu), and substituted phenyl derivatives of Phe, are included in the broad description of the novel inhibitory peptides of the present invention represented by Formula I and its definitions. Thus, the peptides of Formula II and its definitions, including the derivatives of naturally-occurring statine represented by the definitions of the $R^3$ substituent in Formula I, represent preferred peptides of the present invention.

Especially preferred inhibitory peptides of the present invention are the following:
His-Pro-Phe-His-Sta-Leu-Phe-NH$_2$,
iso-Valeryl-His-Pro-Phe-His-Sta-Leu-Phe-NH$_2$,
Acetyl-Pro-Phe-His-Sta-Leu-Phe-NH$_2$,
Acetyl-Phe-His-Sta-Leu-Phe-NH$_2$,
tert-Butyloxycarbonyl-Phe-His-Sta-Leu-Phe-NH$_2$,
tert-Butyloxycarbonyl-His-Pro-Phe-Phe-Sta-Leu-Phe-NH$_2$,
iso-Butyryl-His-Pro-Phe-His-Sta-Ala-Phe-NH$_2$, iso-Butyryl-His—Pro—Phe—His—Sta { Cyclo-hexyl-Phe—NH$_2$ / Ala tert-Butyloxycarbonyl-His-Pro-Phe-His-Sta-Leu-Leu-Leu-OCH$_3$,
tert-Butyloxycarbonyl-His-Pro-Phe-His-Sta-Leu-Tyr-NH$_2$,
iso-Butyryl-His-Pro-Phe-His-Sta-Leu-Phe-Lys-NH$_2$,
tert-Butyloxycarbonyl-His-Pro-Phe-p-I-Phe-Sta-Leu-Phe-NH$_2$,
iso-Valeryl-His-Pro-Phe-His-Sta-Leu-Val-Phe-NH$_2$.

The inhibitory peptides of the present invention may be better appreciated in terms of substrate analogy from the following illustration of Formula I alongside the octapeptide sequence of a portion of the pig renin substrate, which renin cleaves between Leu$^{10}$ and Leu$^{11}$:

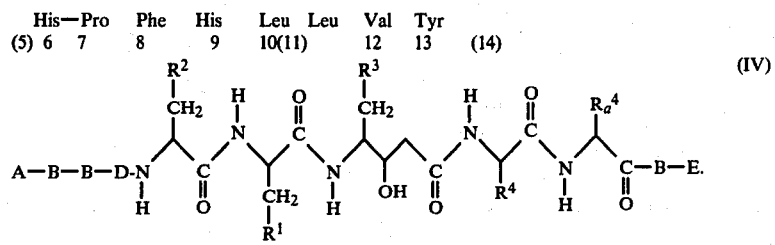

As can be seen, a unique aspect and essential feature of the present invention is the substitution of the single statine amino acid component for the double amino acid sequence: Leu$^{10}$-Leu$^{11}$ in the endogenous pig renin substrate. It is believed that substitution of statine for both leucine amino acids rathen than just one leucine results in an improved substrate analogy due to the greater linear extent of statine as compared to a single leucine component. Thus, statine more closely approximates Leu-Leu in linear extent, and thereby provides a better "fit" to the renin enzyme.

In the endogenous substrate it is also preferred to substitute Leu for Val$^{12}$ and Phe for Tyr$^{13}$ in order to enhance the inhibitory activity of the resulting peptide. Thus, a most preferred inhibitory peptide of the present invention is His-Pro-Phe-His-Sta-Leu-Phe-NH$_2$.

Other specific preferred peptides of the present invention are the following, set out in order by variations in the structure at different positions in the overall peptide sequence, represented by the numbered positions in Formula IV:

| (5) | 6 | 7 | 8 | 9 | (11) | 12 | 13 | (14) |
|---|---|---|---|---|---|---|---|---|
| Variations in position (5): | | | | | 10 | | | |
| Hydrogen — | His—Pro—Phe—His—Sta—Leu—Phe—NH$_2$ | | | | | | | |
| tert-Butyloxycarbonyl- | " | | | | | | | |
| iso-Valeryl- | " | | | | | | | |
| iso-Butyryl- | " | | | | | | | |
| tert-Butyloxycarbonyl- | " | | | | | | | |
| Pro— | " | | | | | | | |
| Variations in position (6): | | | | | 10 | | | |
| Hydrogen— | X*—Pro—Phe—His—Sta—Leu—Phe—NH$_2$ | | | | | | | |
| " | Sar—Pro—Phe—His—Sta—Leu—Phe—NH$_2$ | | | | | | | |
| " | D—His—Pro—Phe—His—Sta—Leu—Phe—NH$_2$ | | | | | | | |
| Acetyl— | X—Pro—Phe—His—Sta—Leu—Phe—NH$_2$ | | | | | | | |
| tert-Butyloxycarbonyl- | " | | | | | | | |
| Phenoxyacetyl— | " | | | | | | | |
| Variations in position (7): | | | | | 10 | | | |
| Hydrogen — | X—X—Phe—His—Sta—Leu—Phe—NH$_2$ | | | | | | | |
| tert-Butyloxycarbonyl- | " | | | | | | | |
| Cyclopentylcarbonyl— | " | | | | | | | |
| Acetyl— | " | | | | | | | |
| iso-Valeryl- | -D-His Pro—Phe—His—Sta—Leu—Phe—NH$_2$ | | | | | | | |
| Variations in position (8): | | | | | 10 | | | |
| iso-Butyryl- | His—Pro—Ala—Phe—Sta—Leu—Phe—NH$_2$ | | | | | | | |

-continued

| (5) | 6 | 7 | 8 | 9 | (11) | 12 | 13 | (14) |
|---|---|---|---|---|---|---|---|---|
| tert-Butyloxycarbonyl- | His—Pro—Phe—His—Sta—Leu—Phe—NH$_2$ with -o-I- on position 10 | | | | | | | |
| Variations in position (9): | | | | | | | | |
| iso-Butyryl- | His—Pro—Phe—Ala—Sta—Leu—Phe—NH$_2$ | | | | | | | |
| tert-Butyloxycarbonyl- | His—Pro—Phe—Phe—Sta—Leu—Phe—NH$_2$ | | | | | | | |
| " | His—Pro—Phe—Phe—Sta—Leu—Phe—NH$_2$ with -p-I- on position 10 | | | | | | | |
| Variations in position (12): | | | | | | | | |
| iso-Butyryl- | His—Pro—Phe—His—Sta—Gly—Phe—NH$_2$ | | | | | | | |
| " | His—Pro—Phe—His—Sta—Ala—Phe—NH$_2$ | | | | | | | |
| " | His—Pro—Phe—His—Sta—Val—Phe—NH$_2$ | | | | | | | |
| " | His—Pro—Phe—His—Sta—Ile—Phe—NH$_2$ | | | | | | | |
| " | His—Pro—Phe—His—Sta—Phe—Phe—NH$_2$ | | | | | | | |
| iso-Butyryl | His—Pro—Phe—His—Sta—Ala—Phe—NH$_2$ with -Cyclohexyl- on position 10 | | | | | | | |
| Variations in position (13): | | | | | | | | |
| iso-Butyryl- | His—Pro—Phe—His—Sta—Leu—Leu—OCH$_3$ | | | | | | | |
| " | His—Pro—Phe—His—Sta—Leu—Tyr—NH$_2$ | | | | | | | |
| tert-Butyloxycarbonyl- | X—X—Phe—His—Sta—Leu—Trp—NH$_2$ | | | | | | | |
| " | X—X—Phe—His—Sta—Leu—Ala—OCH$_3$ | | | | | | | |
| iso-Valeryl—X—X—Phe—His—Sta—Leu—Val—Phe—NH$_2$ | | | | | | | | |
| Variations in position (14): | | | | | 10 | | | |
| iso-Valeryl— | His—Pro—Phe—His—Sta—Leu—Phe—OH | | | | | | | |
| " | His—Pro—Phe—His—Sta—Leu—Phe—OCH$_3$ | | | | | | | |
| iso-Butyryl— | His—Pro—Phe—His—Sta—Leu—Phe—Gly—OH | | | | | | | |
| " | His—Pro—Phe—His—Sta—Leu—Phe—GLY—OCH$_3$ | | | | | | | |
| " | His—Pro—Phe—His—Sta—Leu—Leu—Phe—NH$_2$ | | | | | | | |
| " | His—Pro—Phe—His—Sta—Leu—Leu—Lys—NH$_2$ | | | | | | | |

*X = amino acid absent from position.

The Formula I compounds can be used in the form of salts derived from inorganic or organic acids, and bases. Included among such acid addition salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The novel peptides of the present invention possess an excellent degree of activity in treating renin-associated hypertension and hyperaldosteronism.

For these purposes the compounds of the present invention may be administered parenterally, by inhalation spray, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions may be in the form of a sterile injectable preparation, for example as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The peptides of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order of 2 to 35 grams per day are useful in the treatment of the above indicated conditions. For example, renin-associated hypertension and hyperaldosteronism are effectively treated by the administration of from 30 milligrams to 0.5 grams of the compound per kilogram of body weight per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Thus, in accordance with the present invention there is further provided a pharmaceutical composition for treating renin-associated hypertension and hyperaldosteronism, comprising a pharmaceutical carrier and a therapeutically effective amount of a peptide of the formula:

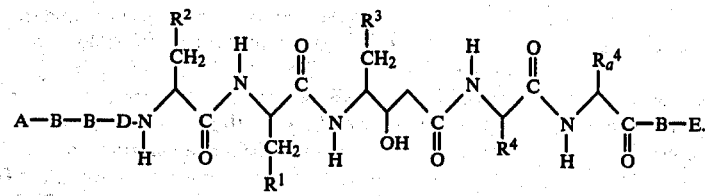

wherein A, B, D, R$^1$, R$^2$, R$^3$, R$^4$, R$_a^4$, and E have the same meanings as recited further above for Formula I; wherein all of the asymmetric carbon atoms have an S configuration, except those of substituents B and D, which may also have the R configuration; and a pharmaceutically acceptable salt thereof.

Also, in accordance with the present invention there is still further provided a method of treating renin-associated hypertension and hyperaldosteronism, comprising administering to a patient in need of such treatment, a therapeutically effective amount of a peptide of the formula:

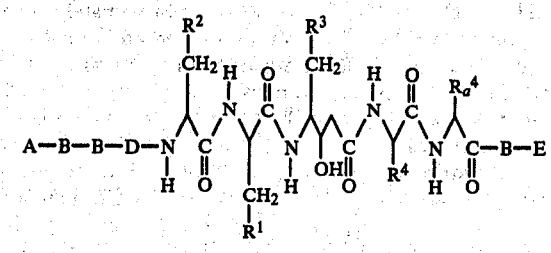

wherein A, B, D, R$^1$, R$^2$, R$^3$, R$^4$, R$_a^4$, and E have the same meaning as recited further above for Formula I; wherein all of the asymmetric carbon atoms have an S configuration, except those of substituents B and D, which may also have the R configuration; and a pharmaceutically acceptable salt thereof.

The renin inhibitory novel peptides of the present invention may also be utilized in diagnostic methods for the purpose of establishing the significance of renin as a causative or contributory factor in hypertension or hyperaldosteronism in a particular patient. For this purpose the novel peptides of the present invention may be administered in a single dose of from 0.1 to 10 mg per kg of body weight.

Both in vivo and in vitro methods may be employed. In the in vivo method, a novel peptide of the present invention is administered to a patient, preferably by intravenous injection, although parenteral administration is also suitable, at a hypotensive dosage level and as a single dose, and there may result a transitory fall in blood pressure. This fall in blood pressure, if it occurs, indicates supranormal plasma renin levels.

An in vitro method which may be employed involves incubating a body fluid, preferably plasma, with a novel peptide of the present invention and, after deproteinization, measuring the amount of angiotensin II produced in nephrectomized, pentolinium-treated rats. Another in vitro method involves mixing the plasma or other body fluid with a novel peptide of the present invention and injecting the mixture into a test animal. The difference in pressor response with and without added peptide is a measure of the renin content of the plasma.

Pepstatin may be employed in the methods described above as an active control. See, e.g., U.S. Pat. Nos. 3,784,686 and 3,873,681 for a description of the use of pepstatin in diagnostic methods of this type.

The novel peptides of the present invention may be prepared in accordance with well-known procedures for preparing peptides from their constituent amino acids, which will be described in more detail below. The unusual amino acid, statine, may be prepared in accordance with the procedure described in Rich et. al., J. Org. Chem. 43: 3624 (1978).

The novel inhibitory peptides of the present invention are prepared by using the solid phase sequential synthesis technique.

In the following description several abbreviated designations are used for the amino acid components, certain preferred protecting groups, reagents and solvents. The meanings of such abbreviated designations are given below in Table I.

TABLE I

| Abbreviated Designation | |
|---|---|
| | Amino Acid |
| Ala | L-alanine |
| Arg | L-arginine |
| Gly | L-glycine |
| His | D or L-histidine |
| Ile | L-isoleucine |
| Leu | L-leucine |
| Lys | L-lysine |
| Met | L-methionine |
| Orn | L-ornithine |
| Phe | L-phenylalanine |
| Pro | D or L-proline |
| Sar | L-sarcosine (N—methylglycine) |
| Ser | L-serine |
| Sta | (3S,4S)-statine |
| Thr | L-threonine |
| Trp | L-tryptophan |
| Tyr | L-tyrosine |
| Val | L-valine |
| | Protecting Groups |
| BOC | tert-butyloxycarbonyl |
| CBZ | benzyloxycarbonyl |
| DNP | dinitrophenyl |
| OMe | methyl ester |
| | Activating Groups |
| HBT | 1-hydroxybenzotriazole |

TABLE I-continued

| Abbreviated Designation | |
|---|---|
| *Condensing Agents* | |
| DCCI | dicyclohexylcarbodiimide |
| DPPA | diphenylphosphorylazide |
| *Reagents* | |
| TEA | triethylamine |
| TFA | trifluoroacetic acid |
| *Solvents* | |
| A | ammonium hydroxide (conc.) |
| AcOH | acetic acid |
| C | chloroform |
| DMF | dimethylformamide |
| E | ethyl acetate |
| M | methanol |
| P | pyridine |
| THF | tetrahydrofuran |
| W | water |

The synthesis of the peptides of the present invention by the solid phase technique is conducted in a stepwise manner on chloromethylated resin. The resin is composed of fine beads (20–70 microns in diameter) of a synthetic resin prepared by copolymerization of styrene with 1–2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as ONp ester, an amino acid azide, and the like. Deprotection and addition of successive amino acids is performed until the desired linear peptide is formed.

The selection is protecting groups is, in part, dictated by particular coupling conditions, in part by the amino acid and peptide components involved in the reaction. Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyoxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e. trifluoroacetic acid, or hydrogen chloride in ethyl acetate).

The OH group of Thr and Ser can be protected by the Bzl group and the -amino group of Lys can be protected by the INOC group or the 2-chlorobenzyloxycarbonyl (2-CL-CBZ) group. Neither group is affected by TFA, used for removing BOC protecting groups. After the peptide is formed, the protective groups, such as 2-Cl-CBZ and Bzl, can be removed by treatment with HF or by catalytic hydrogenation.

After the peptide has been formed on the solid phase resin, it may be removed from the resin by a variety of methods which are well known in the art. For example the peptide may be cleaved from the resin with hydrazine, by ammonia in methanol, or by methanol plus a suitable base.

Preparation of the novel inhibitory peptides of the present invention utilizing the solid phase technique is illustrated in the following examples, which are not, however, intended to be any limitation thereof.

EXAMPLE 1

N-Isovaleryl-L-histidyl-L-prolyl-L-phenylalanyl-L-histidyl-(3S,4S)-statyl-L-leucyl-L-phenylalanine amide The title peptide was prepared by standard solid phase methodology, as described in Erickson and Merrifield, *Proteins,* 3rd et., 2:257–527, 1976, using a Beckman Model 990B peptide synthesizer to carry out the operations according to the attached programs. The starting polymer was BOC-Phe esterified to 2% crosslinked polystyrene-divinylbenzene (6 mmol, 5.00 g). The $N^\alpha$-BOC derivatives of Leu, Sta, His-DNP, Phe, and Pro were coupled using dicyclohexyl-carbodiimide with an equivalent of the additive 1-hydroxybenzotriazole hydrate. The Sta was prepared in accordance with Rich et al., *J. Org. Chem.* 43:3624, 1978. The BOC-group was removed with 40% trifluoroacetic acid. A coupling of 60 minutes followed by a recoupling of 120 minutes (2.5 equivalents each time of BOC-amino acid) were used for each amino acid, except for Sta. These coupling times had been previously demonstrated to give complete coupling (as judged by the method of Kaiser) in this sequence. In order to conserve the amounts of Sta employed, an initial coupling using 1.08 equivalents of $N^\alpha$-BOC-Sta (in 20 ml of 1:1 $CH_2Cl_2$/DMF) for 72 hrs gave approximately 95% complete reaction. The addition of an additional 0.12 equivalents of $N^\alpha$-BOC-Sta plus an equal amount of DCCI to the stirring suspension gave complete coupling after an additional 18 hrs. The N-terminal isovaleryl group was coupled for 60 minutes as the symmetrical anhydride generated in situ from 5.0 equivalents of isovaleric acid and 2.5 equivalents of DCCI. This was followed by a recoupling for 120 minutes using 2.5 equivalents of isovaleric acid, HBT, and DCCI. The DNP protecting groups on His were removed in the final program using two 25-minute treatments with 10% thiophenol in DMF. The finished resin-peptide was dried and suspended in 30 ml methanol containing 1 g ammonium acetate in a 100 ml pressure bottle containing a magnetic stirring bar. The suspension was cooled under nitrogen to −20° C., and anhydrous ammonia was bubbled through the suspension until it was saturated. The pressure bottle was then closed and allowed to warm to room temperature. The suspension was stirred for 72 hrs, after which the pressure valve was carefully opened, allowing the ammonia to escape. The suspension of beads in orange-red solution was filtered and the beads washed. The filtrate and washes were evaporated and the solid dried. This crude product was then partitioned between water (200 ml) and ethyl acetate (200 ml). The ethyl acetate layer was washed three times with 100 ml of a 1% citric acid solution. The product and the acid layer were neutralized with solid sodium hydrogencarbonate. A yellow oil precipitated from the water when it became basic. The now basic water solution and precipitated oil were extracted four times with 100 ml of dichloromethane, and the organic layers were dried and evaporated to give 6.4 g of crude yellow solid. This solid was dissolved in 50 ml of 80:20:2.5:1, chloroform/methanol/water/acetic acid and loaded onto a silica column (E. Merck No. 9385 silica, 0.040–0.063 mm particle size) 8.9×47 cm (ca. 1500 g silica gel) which had been packed in the same solvent. The column was eluted at 18 ml/min with the same solvent and, after 2700 ml, fractions were collected (27 ml each). The pure product was found in fractions 70-110. These fractions were combined and evaporated to a light yellow oil. The oil was dissolved in 20 ml of acetic acid and 300 ml of water were added. The solution was filtered (10μ) and freeze dried to give 4.45 g of light yellow powder.

| TLC: | 80:20:2 | C/M/W | Rf = 0.25 |
|---|---|---|---|
| | 80:20:2:1 | C/M/W/AcOH | Rf = 0.25 |
| | 80:20:2 | C/M/A | Rf = 0.51 |
| | 10:5:1:3 | E/P/AcOH/W | Rf = 0.38 |

For all of the above no impurities were detected at the 1% level, i.e., the product was greater than 99% pure.

| HPLC: Greater than 99% single peak. | | | |
|---|---|---|---|
| Spinco: | His | 1.96 | 89.4% peptide based |
| | Pro | 1.01 | on mol. wt. 1037.3 |
| | Phe | 2.00 | 100% based on |
| | Sta | 1.02 | for. wt. 1157.4 |
| | Leu | 1.02 | |
| | NH$_3$ | 1.25 | |

$^1$H NMR: 300 MHz spectrum consistent with structure proposed; no unexpected peaks.

SCHEDULE OF STEPS FOR 6 MMOL RUN

| Step | Solvent/Reagent | Vol. (ml) | Mix time (min) |
|---|---|---|---|
| Coupling Program 1 | | | |
| 1 | CH$_2$Cl$_2$ | 6 × 60 | 2 |
| 2 | 40% TFA in CH$_2$Cl$_2$ | 1 × 60 | 2 |
| 3 | 40% TFA in CH$_2$Cl$_2$ | 1 × 60 | 25 |
| 4 | CH$_2$Cl$_2$ | 3 × 60 | 2 |
| 5 | 10% TEA in CH$_2$Cl$_2$ | 2 × 60 | 5 |
| 6 | CH$_2$Cl$_2$ | 3 × 60 | 2 |
| 7 | BOC-amino acid, HBT in 1:1 DMF/CH$_2$Cl$_2$ | 40 | 5 |
| 8 | 1.0M DCCI in CH$_2$Cl$_2$ | 15 | 60 |
| 9 | DMF | 1 × 60 | 2 |
| 10 | MeOH | 2 × 60 | 2 |
| 11 | CH$_2$Cl$_2$ | 1 × 60 | 2 |
| Re-Couple Program 2 | | | |
| 1 | CH$_2$Cl$_2$ | 1 × 60 | 2 |
| 2 | 10% TEA in CH$_2$Cl$_2$ | 2 × 60 | 5 |
| 3 | CH$_2$Cl$_2$ | 3 × 60 | 2 |
| 4 | BOC-amino acid, HBT in 1:1 DMF/CH$_2$Cl$_2$ | 40 | 5 |
| 5 | 1.0M DCCI in CH$_2$Cl$_2$ | 15 | 120 |
| 6 | DMF | 1 × 60 | 2 |
| 7 | MeOH | 2 × 60 | 2 |
| 8 | CH$_2$Cl$_2$ | 5 × 60 | 2 |
| Program 3 (DNP removal) | | | |
| 1 | CH$_2$Cl$_2$ | 1 × 60 | 2 |
| 2 | DMF | 2 × 60 | 2 |
| 3 | 10% phenylthiol in DMF | 1 × 60 | 25 |
| 4 | DMF | 1 × 60 | 2 |
| 5 | 10% TEA in CH$_2$Cl$_2$ | 2 × 60 | 2 |
| 6 | DMF | 2 × 60 | 2 |
| 7 | 10% phenylthiol in DMF | 1 × 60 | 25 |

-continued

| Step | Solvent/Reagent | Vol. (ml) | Mix time (min) |
|---|---|---|---|
| 8 | DMF | 3 × 60 | 2 |
| 9 | MeOH | 2 × 60 | 2 |
| 10 | CH$_2$Cl$_2$ | 2 × 60 | 2 |
| 11 | MeOH | 2 × 60 | 2 |
| 12 | CH$_2$Cl$_2$ | 2 × 60 | 2 |
| 13 | MeOH | 2 × 60 | 2 |

EXAMPLES 2–37

Following the standard solid phase methodology described above in Example 1, additional inhibitory peptides of the present invention were prepared, substituting equivalent amounts of the appropriate BOC-amino acid for those utilized in Example 1, and, where necessary, providing N-terminal groups as substitutes for the isovaleryl group in accordance with well established procedures in the art. The peptides prepared are set out in the following table, wherein the subscribed numerical value for each amino acid indicates the results of the Spinco amino acid analysis.

| Example No. | Peptide (5) 6 7 8 9 10(11) 12 13 (14) |
|---|---|
| 2 | H—His—Pro—Phe—His—Sta—Leu—Phe—NH$_2$ 1.01 1.04 1.01 1.01 0.97 0.95 1.01 |
| 3 | BOC—His—Pro—Phe—His—Sta—Leu—Phe—NH$_2$ 1.02 1.04 0.98 1.02 0.98 0.98 |
| 4 | IBU*—His—Pro—Phe—His—Sta—Leu—Phe—NH$_2$ |
| 5 | BOC—Pro—His—Pro—Phe—His—Sta—Leu—Phe—NH$_2$ 1.04 0.97 1.04 1.02 0.97 0.99 1.00 1.02 |
| 6 | H—Pro—Phe—His—Sta—Leu—Phe—NH$_2$ 1.04 1.08 0.94 0.90 0.95 1.08 |
| 7 | Acetyl—Pro—Phe—His—Sta—Leu—Phe—NH$_2$ 0.98 1.00 1.00 1.02 1.00 |
| 8 | BOC—Pro—Phe—His—Sta—Leu—Phe—NH$_2$ 1.09 1.04 0.95 0.94 0.93 1.04 |
| 9 | Phenoxyacetyl—Pro—Phe—His—Sta—Leu—Phe—NH$_2$ 1.02 1.00 0.99 0.99 1.00 |
| 10 | H—Phe—His—Sta—Leu—Phe—NH$_2$ 0.98 1.00 1.03 0.99 |
| 11 | BOC—Phe—His—Sta—Leu—Phe—NH$_2$ 0.98 0.99 1.06 0.98 |
| 12 | Cyclopentylcarbonyl—Phe—His—Sta—Leu—Phe—NH$_2$ 1.02 0.91 1.04 1.02 |
| 13 | IBU—His—Pro—Phe—Ala—Sta—Leu—Phe—NH$_2$ 0.99 0.98 1.01 0.98 1.02 |
| 14 | IBU—His—Pro—Ala—Phe—Sta—Leu—Phe—NH$_2$ 0.95 0.98 0.99 1.04 1.00 1.04 |
| 15 | BOC—His—Pro—Phe—Phe—Sta—Leu—Phe—NH$_2$ 1.01 0.98 1.00 1.00 1.02 1.00 |
| 16 | IBU—His—Pro—Phe—His—Sta—Gly—Phe—NH$_2$ 0.94 1.11 1.00 0.94 1.02 1.00 |
| 17 | IBU—His—Pro—Phe—His—Sta—Ala—Phe—NH$_2$ 1.02 0.96 1.00 1.02 1.00 1.00 |
| 18 | IBU—His—Pro—Phe—His—Sta—Val—Phe—NH$_2$ |
| 19 | BOC—His—Pro—Phe—His—Sta—Ile—Phe—NH$_2$ 1.01 0.99 1.00 1.01 1.00 0.97 1.00 |
| 20 | BOC—His—Pro—Phe—His—Sta—Phe—Phe—NH$_2$ 1.04 1.05 0.98 1.04 0.92 0.98 0.98 |
| 21 | Cyclohexyl-IBU—His—Pro—Phe—His—Sta—Ala—Phe—NH$_2$ 1.00 0.98 1.01 1.00 1.01 |
| 22 | BOC—His—Pro—Phe—His—Sta—Leu—Leu—NH$_2$ 1.04 1.00 0.97 1.04 1.00 0.98 0.98 |
| 23 | BOC—His—Pro—Phe—His—Sta—Leu—Tyr—NH$_2$ 0.99 1.04 0.99 0.99 0.97 1.08 1.13 |
| 24 | BOC—Phe—His—Sta—Leu—Tyr—NH$_2$ 1.00 1.00 1.00 |
| 25 | BOC—Phe—His—Sta—Leu—Ala—OCH$_3$ 1.00 1.01 1.01 0.98 |
| 26 | IVA**—His—Pro—Phe—His—Sta—Leu—Phe—OH |
| 27 | BOC—His—Pro—Phe—His—Sta—Leu—Phe—OCH$_3$ 1.01 1.02 0.99 1.01 1.05 0.93 0.99 |

-continued

| Example No. | Peptide | | | | | | | | | |
|---|---|---|---|---|---|---|---|---|---|---|
| | (5) | 6 | 7 | 8 | 9 | 10 | (11) | 12 | 13 | (14) |
| 28 | IBU—His—Pro—Phe—His—Sta—Leu—Phe—Gly—OH | | | | | | | | | |
| | | 1.02 | 0.97 | 1.01 | 1.02 | | | 0.99 | 1.01 | 0.98 |
| 29 | IBU—His—Pro—Phe—His—Sta—Leu—Phe—Gly—OCH$_3$ | | | | | | | | | |
| | | 1.02 | 0.97 | 1.01 | 1.02 | | | 0.99 | 1.01 | 0.98 |

For the peptides prepared above, various analytical methods were carried out to verify the structure of the peptide products. The following table indicates which methods were employed and summarizes the results where practicable.

| Example No. | Analytical Method | | | | |
|---|---|---|---|---|---|
| | TLC[1] | HPLC[2] | AA[3] | NMR[4] | EA[5] |
| | | (No. of systems) | | | |
| 2 | 95% (3) | 93.2% | X | — | — |
| 3 | 95% (2) | 92.4% | X | — | — |
| 4 | 99% (3) | — | X | X | X |
| 5 | 98% (2) | 98.8% | X | — | — |
| 6 | 90% (2) | — | X | — | — |
| 7 | 95% (2) | 94.2% | X | — | X |
| 8 | 98% | 94% | X | — | — |
| 9 | 97% (2) | 90% | X | — | — |
| 10 | 97% (2) | 92.3% | X | — | X |
| 11 | 97% | 88% | X | — | X |
| 12 | 90% | 80% | X | — | X |
| 13 | 98% (2) | 90.5% | X | X | X |
| 14 | 95% (2) | 96.6% | X | X | X |
| 15 | 95% (2) | 95% | X | — | — |
| 16 | 97% | 90% | — | — | X |
| 17 | 99% (2) | 99% | X | X | X |
| 18 | 98% (3) | 96.1% | X | — | X |
| 19 | 98% | — | X | — | — |
| 20 | 95% (2) | 96.7% | X | — | X |
| 21 | 95% (2) | 98% | X | X | X |
| 22 | 95% | 94.1% | X | — | — |
| 23 | 95% (2) | — | X | — | — |
| 24 | 95% | 95% | X | X | — |
| 25 | 95% | 98% | X | X | — |
| 26 | 95% (3) | 80% | — | — | X |
| 27 | 98% | 99% | X | — | — |
| 28 | 98% (2) | 96.7% | X | — | X |
| 29 | 97% (3) | 95.8% | X | — | X |
| 30 | 98% | 98% | X | — | — |
| 31 | 99% (3) | 95.0% | X | — | X |
| 32 | 95% (2) | 97.0% | X | X | X |
| 33 | 95% (2) | 94.7% | X | X | — |
| 34 | 95% (2) | 93.6% | X | X | X |
| 35 | 95% (2) | 95.3% | X | X | X |
| 36 | 95% (2) | 94.0% | X | X | X |
| 37 | 95% (2) | 98.3% | X | X | X |

[1]TLC = thin layer chromatography on silica gel; visualization by reagents which tend to detect peptides; no. of systems refers to number of different solvent mixtures used to elute chromatograms; % refers to estimated purity.
[2]HPLC = high pressure liquid chromatography; detection by ultraviolet absorption at 240 nm or 210 nm; chromatography is reverse phase, i.e., non-polar elution from non-polar support; % refers to purity, but method tends to overestimate non-peptide impurities.
[3]AA = amino acid analysis; peptides are hydrolyzed to their component amino acids, which are then quantitatively measured; values should be 1.00 ± 0.03.
[4]NMR = nuclear magnetic resonance spectroscopy at 300 MHz or 360 MHz for protons; X = spectrum consistent with structure; — = not performed.
[5]EA = elemental analysis for C, H, and N; X = analysis consistent with structure plus added solvent; — = not performed.

EXAMPLE 38

Hog Renin Inhibition

An assay was carried out in order to determine the inhibitory potency of the peptides of the present invention. The assay measured the inhibition of hog kidney renin, and was in accordance with the procedure described in Rich et al., *J. Med. Chem.* 23:27, 1980, except that a pH of 7.3 was used. The results of the assay, illustrated in the table below, was expressed as I$_{50}$ values, which refers to the concentration of peptide inhibitor necessary to produce 50% inhibition of renin activity. This I$_{50}$ value is obtained typically by plotting data from four inhibitor concentrations. Pepstatin was used as an active control.

| Peptide | I$_{50}$(M) |
|---|---|
| H—His—Pro—Phe—His—Sta—Leu—Phe—NH$_2$ | $2.0 \times 10^{-8}$ |
| iso-Valeryl—His—Pro—Phe—His—Sta—Leu—Phe—NH$_2$ | $3.0 \times 10^{-8}$ |
| Acetyl—Pro—Phe—His—Sta—Leu—Phe—NH$_2$ | $3.7 \times 10^{-8}$ |
| Acetyl—Phe—His—Sta—Leu—Phe—NH$_2$ | |
| BOC—Phe—His—Sta—Leu—Phe—NH$_2$ | $3.6 - 10^{-8}$ |
| BOC—His—Pro—Phe—Phe—Sta—Leu—Phe—NH$_2$ | $2.0 \times 10^{-8}$ |
| IBU—His—Pro—Phe—His—Sta—Ala—Phe—NH$_2$ | $3.7 \times 10^{-8}$ |
| IBU—His—Pro—Phe—His—Sta—Ala—Phe—NH$_2$ | $2.0 \times 10^{-8}$ |
| BOC—His—Pro—Phe—His—Sta—Leu—Leu—OCH$_3$ | $2.3 \times 10^{-8}$ |
| BOC—His—Pro—Phe—His—Sta—Leu—Tyr—NH$_2$ | $2.6 \times 10^{-8}$ |
| IBU—His—Pro—Phe—His—Sta—Leu—Phe—Lys—NH$_2$ | $2.3 \times 10^{-8}$ |
| Sar—Pro—Phe—His—Sta—Leu—Phe—NH$_2$ | $6.6 \times 10^{-8}$ |
| D-His—Pro—Phe—His—Sta—Leu—Phe—NH$_2$ | $4.9 \times 10^{-8}$ |
| IVA—His—D—Pro—Phe—His—Sta—Leu—Phe—NH$_2$ | $5.8 \times 10^{-8}$ |
| BOC—His—Pro—o-I—Phe—His—Sta—Leu—Phe—NH$_2$ | $4.2 \times 10^{-8}$ |
| BOC—His—Pro—Phe—p-I—Phe—Sta—Leu—Phe—NH$_2$ | $8.1 \times 10^{-9}$ |
| IVA—His—Pro—Phe—His—Sta—Leu—Val—Phe—NH$_2$ | $4.6 \times 10^{-8}$ |
| Pepstatin (iso-valeryl-Val—Val—Sta—Ala—Sta) | $1.0 \times 10^{-6}$ |

EXAMPLE 39

Hog Renin and Human Renin Inhibition

In order to illustrate the correlation between hog renin inhibition and human renin inhibition by a single peptide entity, two of the peptide inhibitors evaluated in the hog renin inhibition assay described above in Example 38 were further evaluated in human renin assay based on the method of Haber et al., *J. Clin. Endocrinol.* 29:1349, 1969. This method employs a radioimmunoassay technique to measure the amount of angiotensin I product of renin cleavage of its substrate. Human plasma (lyophilized) was used as the source of human substrate and human renin. I$_{50}$ values were obtained by plotting data at several inhibitor concentrations. The comparative results are illustrated below. Pepstatin was used as an active control.

| Peptide | I$_{50}$(M) | |
|---|---|---|
| | Hog renin | Human renin |
| iso-Valeryl—His—Pro—Phe—His—Sta—Leu—Phe—NH$_2$ | $3.0 \times 10^{-8}$ | $1.8 \times 10^{-8}$ |
| iso-Butyryl—His—Pro—Phe—His—Sta—Ala—Phe—NH$_2$ | $3.7 \times 10^{-8}$ | $4.2 \times 10^{-8}$ |
| Pepstatin(iso-valeryl-Val—Val—Sta—Ala—Sta) | $1.0 \times 10^{-6}$ | $1.0 \times 10^{-6}$ (20% inhibition at $1.0 \times 10^{-6}$) |

What is claimed is:
1. A peptide of the formula:

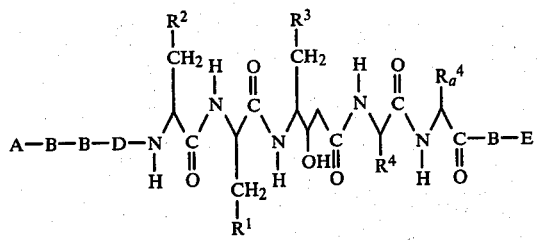

wherein:
A is hydrogen;

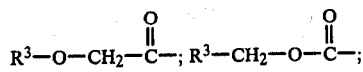

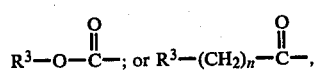

where n is 0 to 5 and $R^3$ has the same meaning as set out further below, and may additionally be hydrogen;

B is absent; glycyl; sarcosyl; or

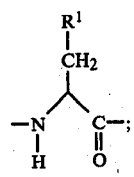

D is absent; or

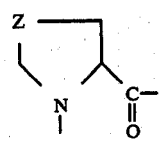

where Z is $(CH_2)_n$ and n is 1 or 2; or —S—;

$R^1$ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl;

$R^2$ is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;

$R^3$ is $C_{3-6}$ alkyl; $C_{3-7}$ cycloalkyl; phenyl; or phenyl mono-substituted with a member selected from the group consisting of methyl, trifluoromethyl, hydroxy, methoxy, fluoro, chloro, bromo, and iodo;

$R^4$ and $R_a^4$ are independently hydrogen; or

where $R^5$ is hydrogen; $C_{1-4}$ alkyl; hydroxy; or $C_{3-7}$ cycloalkyl; and

E is OR; NHR, or $N(R)_2$, where each R may be the same or different and is hydrogen or $C_{1-4}$ alkyl;

wherein all of the asymmetric carbon atoms have an S configuration, except those of substituents B and D, which may also have the R configuration; and a pharmaceutically acceptable salt thereof.

2. A peptide according to claim 1 wherein the peptide is His-Pro-Phe-His-Sta-Leu-Phe-$NH_2$.

3. A peptide according to claim 1 wherein the peptide is iso-valeryl-His-Pro-Phe-His-Sta-Leu-Phe-$NH_2$.

4. A peptide according to claim 1 wherein the peptide is acetyl-Pro-Phe-His-Sta-Leu-Phe-$NH_2$.

5. A peptide according to claim 1 wherein the peptide is acetyl-Phe-His-Sta-Leu-Phe-$NH_2$.

6. A peptide according to claim 1 wherein the peptide is tert-butyloxycarbonyl-Phe-His-Sta-Leu-Phe-$NH_2$.

7. A peptide according to claim 1 wherein the peptide is tert-butyloxycarbonyl-His-Pro-Phe-Phe-Sta-Leu-Phe-$NH_2$.

8. A peptide according to claim 1 wherein the peptide is iso-butyryl-His-Pro-Phe-His-Sta-Ala-Phe-$NH_2$.

9. A peptide according to claim 1 wherein the peptide is iso-butyryl-His-Pro-Phe-His-Sta-Cyclo-hexyl-Ala-Phe-$NH_2$.

10. A peptide according to claim 1 wherein the peptide is tert-butyloxycarbonyl-His-Pro-Phe-His-Sta-Leu-Leu-$OCH_3$.

11. A peptide according to claim 1 wherein the peptide is tert-butyloxycarbonyl-His-Pro-Phe-His-Sta-Leu-Tyr-$NH_2$.

12. A peptide according to claim 1 wherein the peptide is iso-butyryl-His-Pro-Phe-His-Sta-Leu-Phe-Lys-$NH_2$.

13. A peptide according to claim 1 wherein the peptide is tert-butyloxycarbonyl-His-Pro-Phe-p-I-Phe-Sta-Leu-Phe-$NH_2$.

14. A peptide according to claim 1 wherein the peptide is iso-valeryl-His-Pro-Phe-His-Sta-Leu-Val-Phe-$NH_2$.

15. A pharmaceutical composition for treating renin-associated hypertension, comprising a pharmaceutical carrier and a therapeutically effective amount of a peptide of the formula:

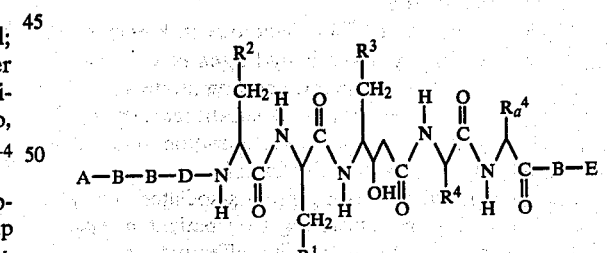

wherein:
A is hydrogen;

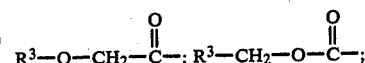

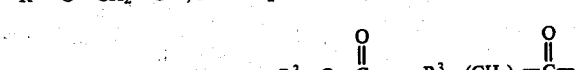

where n is 0 to 5 and $R^3$ has the same meaning as set out further below, and may additionally be hydrogen;

B is absent; glycyl; sarcosyl; or

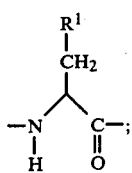

D is absent; or

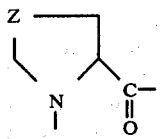

where Z is $(CH_2)_n$ and n is 1 or 2; or —S—;

$R^1$ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl;

$R^2$ is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;

$R^3$ is $C_{3-6}$ alkyl; $C_{3-7}$ cycloalkyl; phenyl; or phenyl mono-substituted with a member selected from the group consisting of methyl, trifluoromethyl, hydroxy, methoxy, fluoro, chloro, bromo, and iodo;

$R^4$ and $R_a^4$ are independently hydrogen; or

where $R^5$ is hydrogen; $C_{1-4}$ alkyl; hydroxy; or $C_{3-7}$ cycloalkyl; and

E is OR; NHR, or $N(R)_2$, where each R may be the same or different and is hydrogen or $C_{1-4}$ alkyl;

wherein all of the asymmetric carbon atoms have an S configuration, except those of substituents B and D, which may also have the R configuration; and a pharmaceutically acceptable salt thereof.

16. A method of treating renin-associated hypertension comprising administering to a patient in need of such treatment, a therapeutically effective amount of a peptide of the formula:

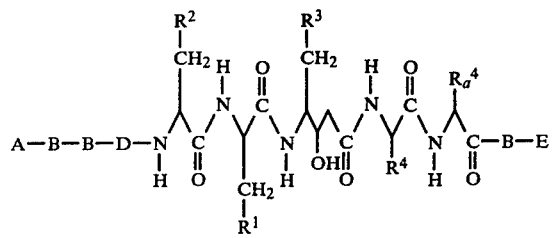

wherein:

A is hydrogen;

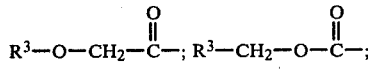

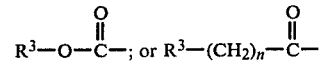

where n is 0 to 5 and $R^3$ has the same meaning as set out further below, and may additionally be hydrogen;

B is absent; glycyl; sarcosyl; or

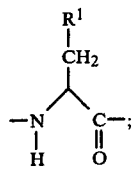

D is absent; or

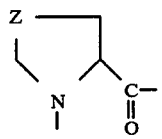

where Z is $(CH_2)_n$ and n is 1 or 2; or —S—;

$R^1$ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl;

$R^2$ is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;

$R^3$ is $C_{3-6}$ alkyl; $C_{3-7}$ cycloalkyl; phenyl; or phenyl mono-substituted with a member selected from the group consisting of methyl, trifluoromethyl, hydroxy, methoxy, fluoro, chloro, bromo, and iodo;

$R^4$ and $R_a^4$ are independently hydrogen; or

where $R^5$ is hydrogen; $C_{1-4}$ alkyl; hydroxy; or $C_{3-7}$ cycloalkyl; and

E is OR; NHR, or $N(R)_2$, where each R may be the same or different and is hydrogen or $C_{1-4}$ alkyl;

wherein all of the asymmetric carbon atoms have an S configuration, except those of substituents B and D, which may also have the R configuration; and a pharmaceutically acceptable salt thereof.

17. A pharmaceutical composition for treating renin-associated hyperaldosteronism, comprising a pharmaceutical carrier and a therapeutically effective amount of a peptide of the formula

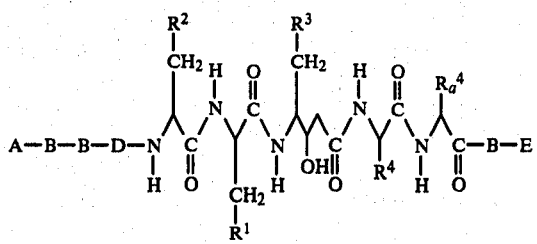

wherein:
A is hydrogen;

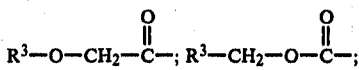

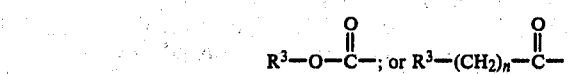

where n is 0 to 5 and $R^3$ has the same meaning as set out further below, and may additionally be hydrogen;
B is absent; glycyl; sarcosyl; or

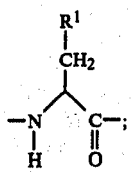

D is absent; or

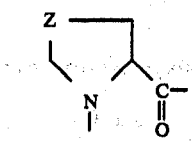

where Z is $(CH_2)_n$ and n is 1 or 2; or —S—;
$R^1$ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl;
$R^2$ is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;
$R^3$ is $C_{3-6}$ alkyl; $C_{3-7}$ cycloalkyl; phenyl; or phenyl mono-substituted with a member selected from the group consisting of methyl, trifluoromethyl, hydroxy, methoxy, fluoro, chloro, bromo, and iodo;
$R^4$ and $R_a^4$ are independently hydrogen; or

where $R^5$ is hydrogen; $C_{1-4}$ alkyl; hydroxy; or $C_{3-7}$ cycloalkyl; and

E is OR; NHR, or $N(R)_2$, where each R may be the same or different and is hydrogen or $C_{1-4}$ alkyl;
wherein all of the asymmetric carbon atoms have an S configuration, except those of substituents B and D, which may also have the R configuration; and a pharmaceutically acceptable salt thereof.

18. A method of treating renin-associated hyperaldosteronism, comprising administering to a patient in need of such treatment, a therapeutically effective amount of a peptide of the formula:

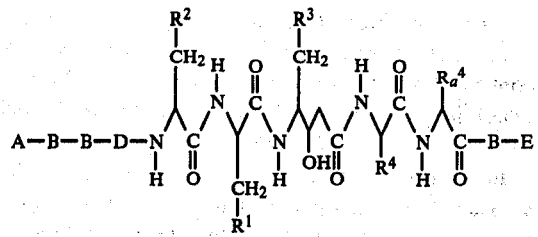

wherein:
A is hydrogen;

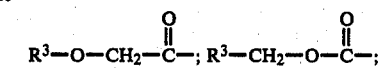

where n is 0 to 5 and $R^3$ has the same meaning as set out further below, and may additionally be hydrogen;
B is absent; glycyl; sarcosyl; or

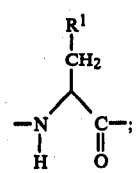

D is absent; or

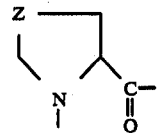

where Z is $(CH_2)_n$ and n is 1 or 2; or —S—;
$R^1$ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl;
$R^2$ is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;
$R^3$ is $C_{3-6}$ alkyl; $C_{3-7}$ cycloalkyl; phenyl; or phenyl mono-substituted with a member selected from the group consisting of methyl, trifluoromethyl, hydroxy, methoxy, fluoro, chloro, bromo, and iodo; $R^4$ and $R_a^4$ are independently hydrogen; or

where $R^5$ is hydrogen; $C_{1-4}$ alkyl; hydroxy; or $C_{3-7}$ cycloalkyl; and

E is OR; NHR, or $N(R)_2$, where each R may be the same or different and is hydrogen or $C_{1-4}$ alkyl; wherein all of the asymmetric carbon atoms have an S configuration, except those of substituents B and D, which may also have the R configuration; and a pharmaceutically acceptable salt thereof.

19. A method of determining the presence of renin-associated hypertension in a patient, comprising administering to such a patient, at a hypotensive dosage level and as a single dose, a peptide of the formula:

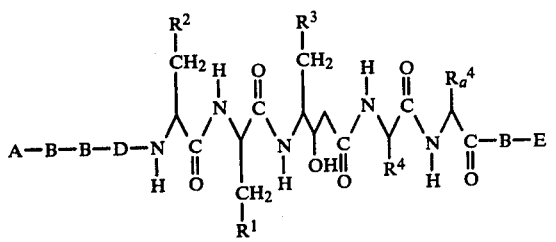

wherein:

A is hydrogen;

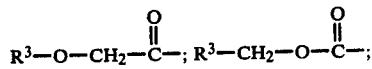

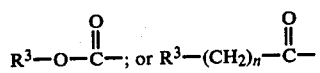

where n is 0 to 5 and $R^3$ has the same meaning as set out further below, and may additionally be hydrogen;

B is absent; glycyl; sarcosyl; or

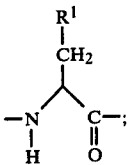

D is absent; or

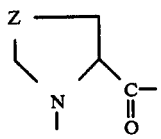

where Z is $(CH_2)_n$ and n is 1 or 2; or —S—;

$R^1$ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl;

$R^2$ is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;

$R^3$ is $C_{3-6}$ alkyl; $C_{3-7}$ cycloalkyl; phenyl; or phenyl mono-substituted with a member selected from the group consisting of methyl, trifluoromethyl, hydroxy, methoxy, fluoro, chloro, bromo, and iodo;

$R^4$ and $R_a^4$ are independently hydrogen; or

where $R^5$ is hydrogen; $C_{1-4}$ alkyl; hydroxy; or $C_{3-7}$ cycloalkyl; and

E is OR; NHR, or $N(R)_2$, where each R may be the same or different and is hydrogen or $C_{1-4}$ alkyl; wherein all of the asymmetric carbon atoms have an S configuration, except those of substituents B and D, which may also have the R configuration; and a pharmaceutically acceptable salt thereof; followed by monitoring of said patient's blood pressure.

* * * * *